(12) United States Patent
Halbert et al.

(10) Patent No.: US 10,925,763 B2
(45) Date of Patent: Feb. 23, 2021

(54) STENT DELIVERY CATHETER WITH CONVERTIBLE LIVING-HINGE FOR SLOW TO FAST RETRACTION

(71) Applicant: Cardinal Health Switzerland 515 GmbH, Baar (CH)

(72) Inventors: Phillip Halbert, Milpitas, CA (US); Matt Gill, Milpitas, CA (US)

(73) Assignee: CARDINAL HEALTH SWITZERLAND 515 GMBH, Baar (CH)

( * ) Notice: Subject to any disclaimer, the term of this patent is extended or adjusted under 35 U.S.C. 154(b) by 147 days.

(21) Appl. No.: 16/128,168

(22) Filed: Sep. 11, 2018

(65) Prior Publication Data
US 2019/0076281 A1 Mar. 14, 2019

Related U.S. Application Data

(60) Provisional application No. 62/558,336, filed on Sep. 13, 2017.

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05); *A61F 2220/0091* (2013.01)

(58) Field of Classification Search
CPC .. A61F 2/966; A61F 2/95; A61F 2/962; A61F 2/2466; A61F 2002/011; A61F 2002/9517; A61F 2220/0091; A61B 17/12022
See application file for complete search history.

(56) References Cited

U.S. PATENT DOCUMENTS

| | | | |
|---|---|---|---|
| 4,580,568 A | 4/1986 | Gianturco | |
| 4,732,152 A | 3/1988 | Wallsten et al. | |
| 5,601,568 A | 2/1997 | Chevillon et al. | |
| 6,019,778 A | 2/2000 | Wilson et al. | |
| 6,939,352 B2 | 9/2005 | Buzzard et al. | |
| 7,967,829 B2 | 6/2011 | Gunderson et al. | |
| 2013/0150829 A1 | 6/2013 | Fargahi et al. | |
| 2017/0156906 A1 | 6/2017 | Green et al. | |
| 2018/0318521 A1* | 11/2018 | Wendland | A61M 5/20 |

FOREIGN PATENT DOCUMENTS

| | | |
|---|---|---|
| JP | 2003159334 A | 6/2003 |
| JP | 2007508045 A | 4/2005 |

OTHER PUBLICATIONS

International Search Report and Written Opinion for Application No. PCT/IB2018/001115, dated Jan. 22, 2019, 13 pages.
(Continued)

*Primary Examiner* — Wade Miles
*Assistant Examiner* — Mohammed S Adam
(74) *Attorney, Agent, or Firm* — Dergosits & Noah LLP; Todd A. Noah (57) ABSTRACT

Various embodiments for a stent delivery device that utilizes a lost motion technique via a living connected to two cantilever arms for slow retraction of an outer sheath and an actuator member coupled to the two arms for fast retraction of the outer sheath during delivery of a self-expanding implantable device such as a stem or stent graft.

16 Claims, 7 Drawing Sheets

(56) References Cited

OTHER PUBLICATIONS

International Preliminary Report on Patentability in International Patent Application No. PCT/IB2018/001115, dated Mar. 17, 2020.
Search Report from corresponding Japanese Patent Application No. 2019565369, dated Nov. 5, 2020.
Notice of Refusal from corresponding Japanese Patent Application No. 2019565369, dated Nov. 10, 2020.

* cited by examiner

STENT DELIVERY CATHETER WITH CONVERTIBLE LIVING-HINGE FOR SLOW TO FAST RETRACTION

PRIORITY CLAIM AND RELATED APPLICATIONS

This application claims priority under 35 U.S.C. § 119 or the Paris Convention from U.S. Provisional Patent Application 62/558,336 filed Sep. 13, 2017, the entire contents of which is incorporated herein by reference as if set forth in full herein.

BACKGROUND

It is well known to employ various intravascular endoprostheses delivered percutaneously for the treatment of diseases of various body vessels. These types of endoprosthesis are commonly referred to as "stents". A stent (which includes covered stents or stent-graft) is a generally longitudinal tubular device of biocompatible material, such as stainless steel, cobalt-chromium, nitinol or biodegradable materials, having holes or slots cut therein to define a flexible framework so they can be radially expanded, by a balloon catheter or the like, or alternately self-expanded due to its shape memory characteristic of the material within a biological vessel. The stents are usually configured as a series of hoops with each defined by cylinder-like framework. The framework is usually a series of alternating sequence of struts with a vertex between each pair of struts and configured so that the vertex of one hoop facing a vertex of the adjacent hoops may be connected together. The struts are configured to move and thereby allow the stent to be compressed or "crimped" into a smaller outer diameter so that they can be mounted inside a delivery system.

The delivery systems are used to convey the stent to a desired location for treatment, and then deploy them in position. Many such stents are resiliently compressed to a smaller initial size for containment, protection, storage and eventual delivery from inside a catheter system. Upon deployment, the stents may resiliently self-expand to a larger deployed size.

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10 of Wilson, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al., on Mar. 22, 1988.

In operation, these known stent delivery systems are generally advanced within a body of a patient along a desired vascular path or other body passageway, until the stent within the catheter system is located at a desired site for treatment. While watching the relative positions of the stent and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a stent as the outer sheath is retracted. This gradual expansion presents an opportunity for a possible reverse "watermelon-seed" phenomenon to occur. This reverse watermelon-seed effect may cause the resilient stent to tend to push the outer sheath back in a proximal direction with a force that tends to change as the sheath is progressively retracted.

As a result, the physician may need to accurately hold the two proximal hubs in a specific relative position, holding them against this expansion force, while attempting to very accurately position the stent up until contact with the anatomy. One of the possibilities that may affect the positioning of the deployed stent is that the inner shaft should preferably be held stationary in the desired position. If the physician's hand that holds the inner shaft hub does inadvertently move during deployment, it is possible that the stent may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the stent may be adjusted up until the point at which a portion of the expanding portion of the stent touches the sidewalls of the body passage, so that the position of the stent should preferably be carefully adjusted until immediately before a portion of the stent touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated stent.

SUMMARY OF THE DISCLOSURE

Applicant has devised a stent delivery system in the form of a housing coupled to a catheter tip. The catheter tip is coupled to an inner shaft and an outer sheath with a stent disposed between the inner shaft and the outer sheath. The inner shaft and the outer sheath extends from a distal end to a proximal end. The housing extends along a longitudinal axis from a first end to a second end. The housing defines a slot in the housing along the longitudinal axis. A first arm is coupled to the housing with a portion of the first arm disposed in the slot. A second arm is connected to the first arm via a living hinge. The second arm is coupled to the outer sheath. The second arm having a portion disposed in the slot. An actuator member is coupled to the second arm.

A method of delivering a self-expanding stent to selected location in a body vessel can be achieved by: moving a stent to a selected location in a body vessel, the stent being disposed adjacent a catheter tip and confined between an inner shaft and an outer sheath at a distal end of a delivery system; depressing an actuator orthogonally with respect to a longitudinal axis to translate the outer sheath over a first range of travel along a longitudinal axis to expose a portion of the stent; and sliding the actuator along the longitudinal axis to translate the outer sheath over a second range of travel along the longitudinal axis to completely deploy the stent.

For each of the embodiments described above, the following features can be utilized in various permutations with each of the embodiments. For example, the first arm is coupled to an interior wall proximate the first end of the housing; the second arm is coupled to a pivot mount connected to the outer sheath; the pivot mount is confined to translate in the slot along the longitudinal axis; a luer port is coupled to the outer sheath at the second end of the housing; the outer sheath is configured to translate along the longitudinal axis over a first range of travel as the first and second arms pivot about the living hinge and the outer sheath is configured to translate along the longitudinal axis over a second range of travel when the first and second arms are substantially collinear with the living hinge; the actuator member is configured to move orthogonally to the longitudinal axis over the first range of travel; the actuator member is configured to cause less translation of the outer sheath over the first range of travel as compared to the second range of travel for a given amount of actuator member movement.

These and other embodiments, features and advantages will become apparent to those skilled in the art when taken with reference to the following more detailed description of the exemplary embodiments of the invention in conjunction with the accompanying drawings that are first briefly described. As well, it is intended that these embodiments, features and advantages may be claimed in this or additional applications for patents.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values 10% of the recited value, e. g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "stent" is intended to encompass an uncovered framework as well as one that is covered by a suitable material (e.g., stent-graft). The term "proximal" is used to denote the location closer to the operator and "distal" is used to denote a location further away from the operator or the health care provider.

Figure 1:
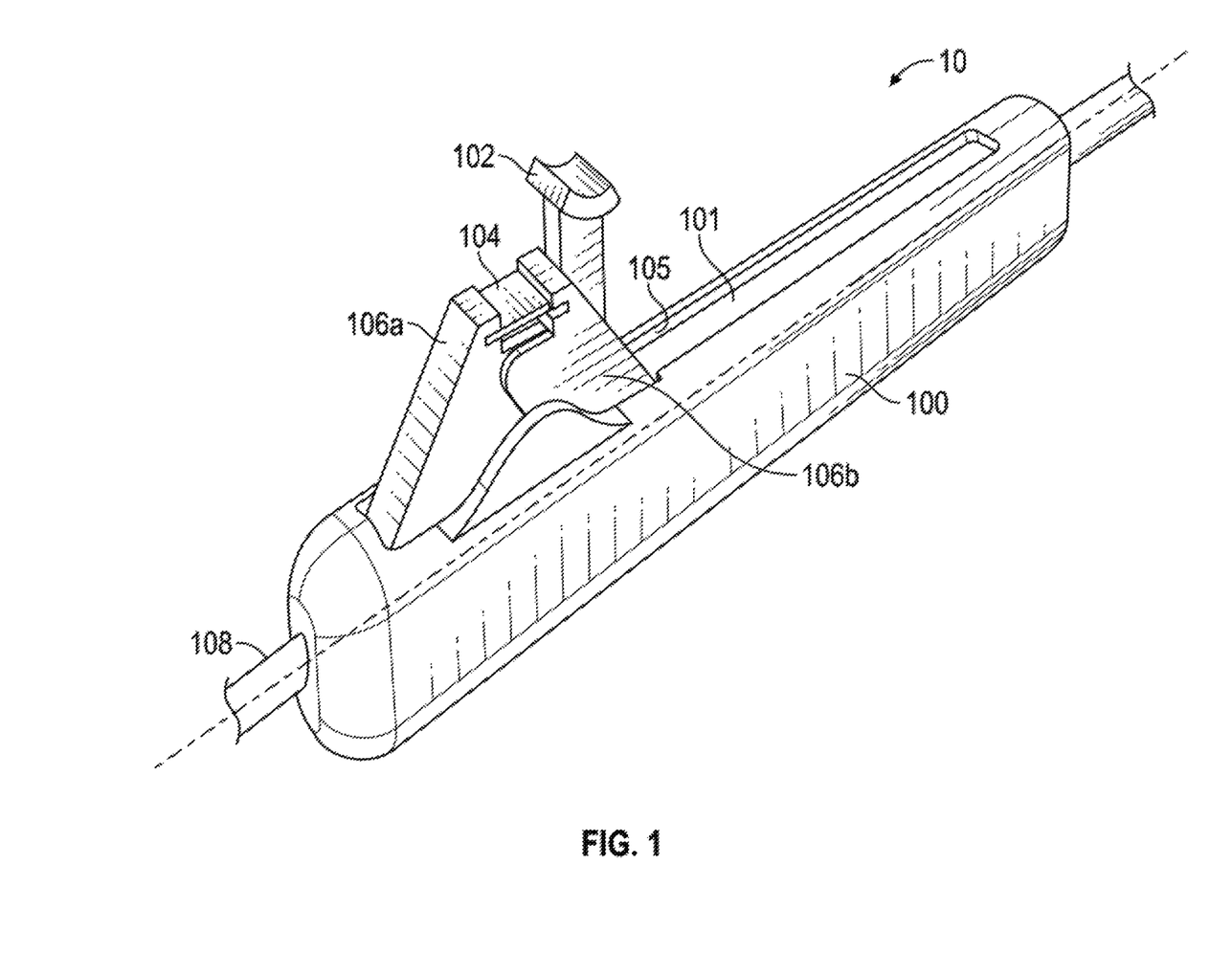
FIG. 1 illustrates a perspective view of a handle according to an embodiment.
Figure 2A:
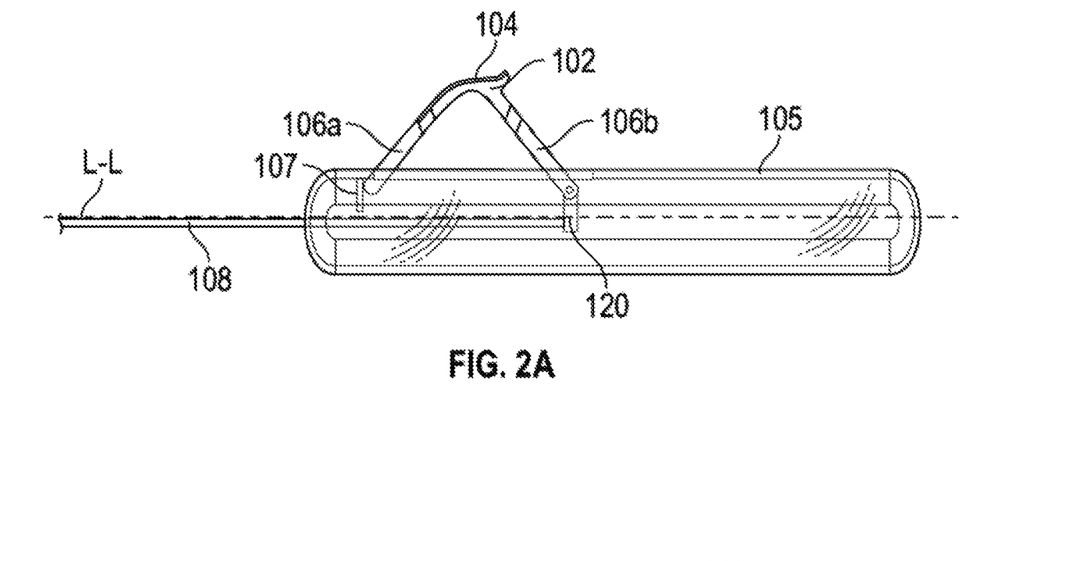
FIGS. 2A, 2B, and 2C illustrate the internal operation of the handle in FIG. 1.
Figure 5A:
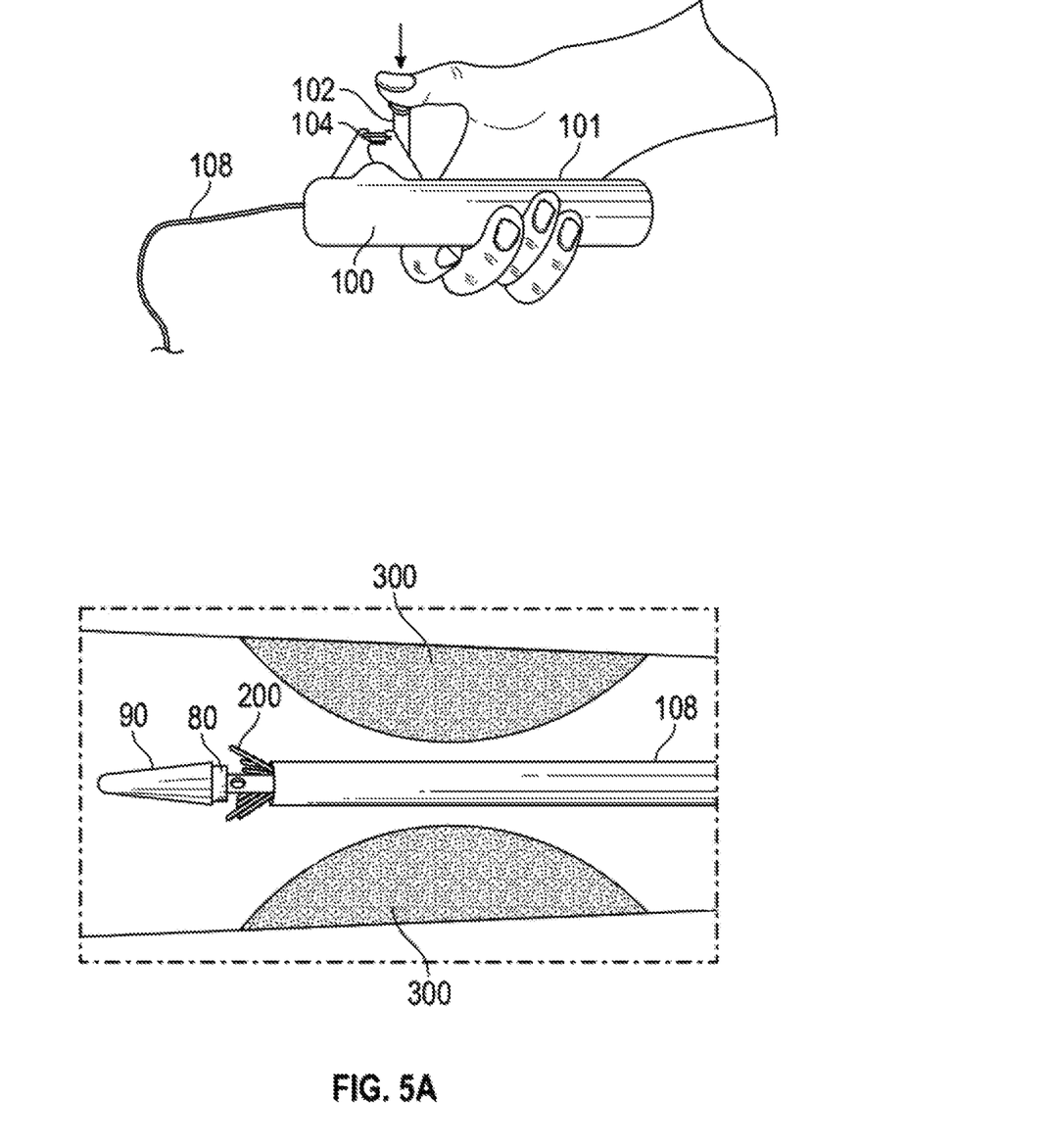
FIGS. 5A, 5B, and 5C illustrate the operation of the system, according to an embodiment.

Referring now to the figures wherein like numerals indicate the same element throughout the views, there is shown in FIG. 1 a portion of the delivery system 10 in the form of a handle that defines a housing 100 coupled to a catheter tip 90 (FIG. 5A). The catheter tip 90 is coupled to an inner shaft 80 and an outer sheath 108 with a stent 200 disposed between the inner shaft 80 and the outer sheath 108. The inner shaft 80 and the outer sheath 108 extends from a distal end to a proximal end. The housing 100 extends along a longitudinal axis L-L from a first end to a second end. The housing 100 defines a slot 101 in the housing along the longitudinal axis L-L. A first arm 106a is coupled to the housing 100 with a portion of the first arm 106a disposed in the slot 101. A second arm 106b is connected to the first arm 106a via a living hinge 104. The second arm 106b is coupled to the outer sheath 108 (FIG. 2A). The second arm 106b has a portion disposed in the slot 101. An actuator member 102 is coupled to the second arm 106b.

As shown in FIG. 2A, the first arm 106a relies on the inherent resiliency of the living hinge 104 to allow the first arm 106a to be coupled or pressed against an interior abutment 107 in the housing 100. Alternatively, the first arm 106a can be pivotably mounted via pivot pins for greater retention of the first arm 106a in the housing 100.

On the other hand, the second arm 106b is coupled to a pivot mount 120 which is connected to the outer sheath 108, so that relative longitudinal movement of pivot mount 120 within housing 100 causes a corresponding longitudinal movement of outer sheath 108 while inner shaft 80 is restrained by a suitable coupling to housing 100 so that it is maintained in a substantially fixed position. As will be appreciated, longitudinal movement of outer sheath 108 in a proximal direction relative to inner shaft 80 exposes and deploys stent 200 (FIGS. 5A and 5B) as will be described in further detail below. Other forms of suitable mounts can be utilized as long as such mount(s) allow for rotation of the arm 106b. As shown in FIG. 2A, rail 105 can be provided in slot 101 to ensure that the arm 106b is confined to translate along axis L-L without detaching from the handle 100.

For purposes of flushing or insertion of a guidewire or other accessories into the body vessel 300, a luer port 110 is provided at the proximal end of the housing 100. The port 110 is coupled to the outer sheath 108 by a suitable coupling including a slip coupling to allow the outer sheath 108 to slide over a smaller tubular member (not shown) of the luer port 110.

Figure 2B:
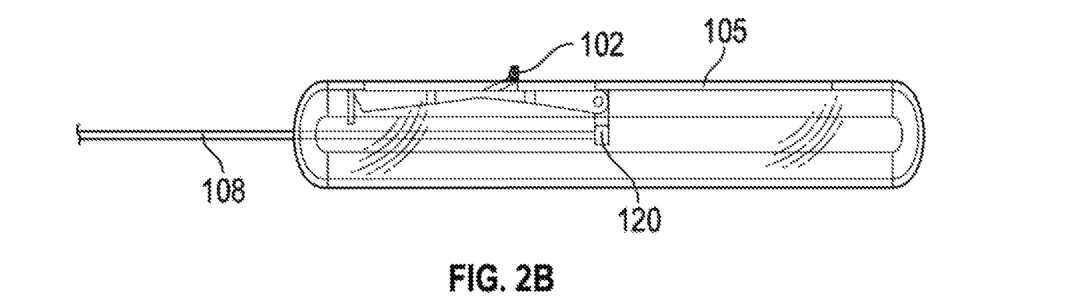
Figure 2C:
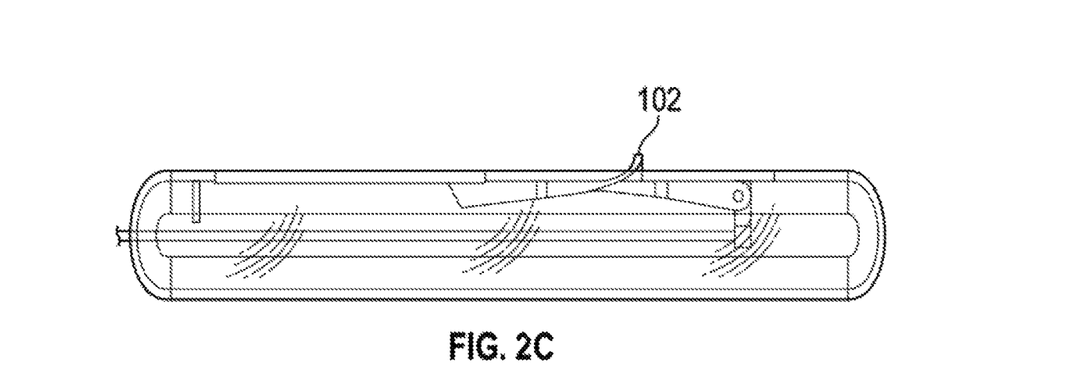
Figure 3A:
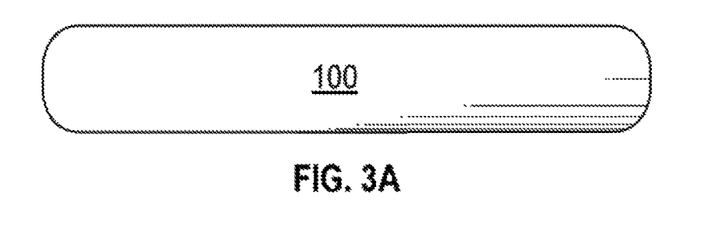
FIGS. 3A, 3B, 3C, 3D and 3E illustrates yet other permutations of the handle in FIG. 1.
Figure 3B:
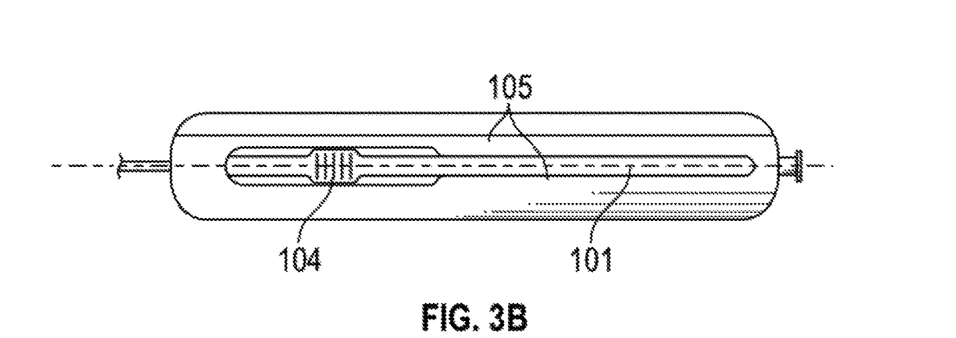
Figure 3C:
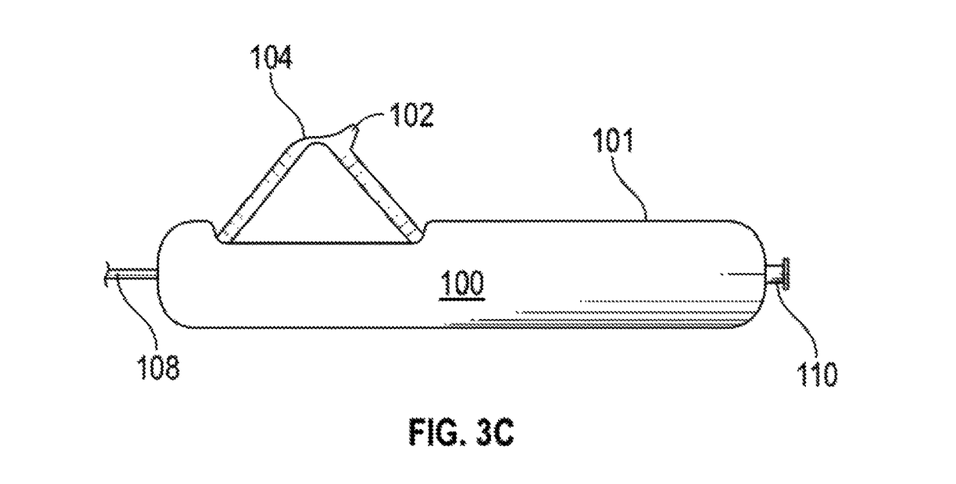
Figure 3D:
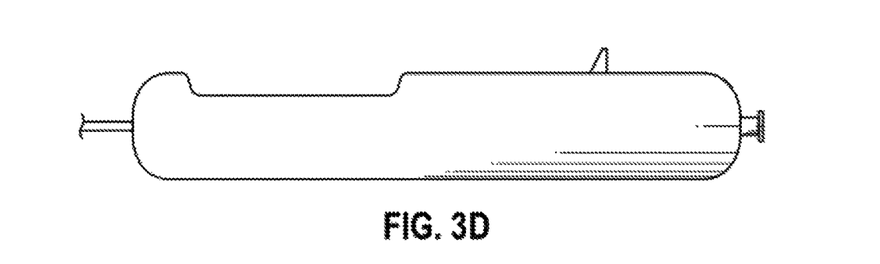
Figure 3E:
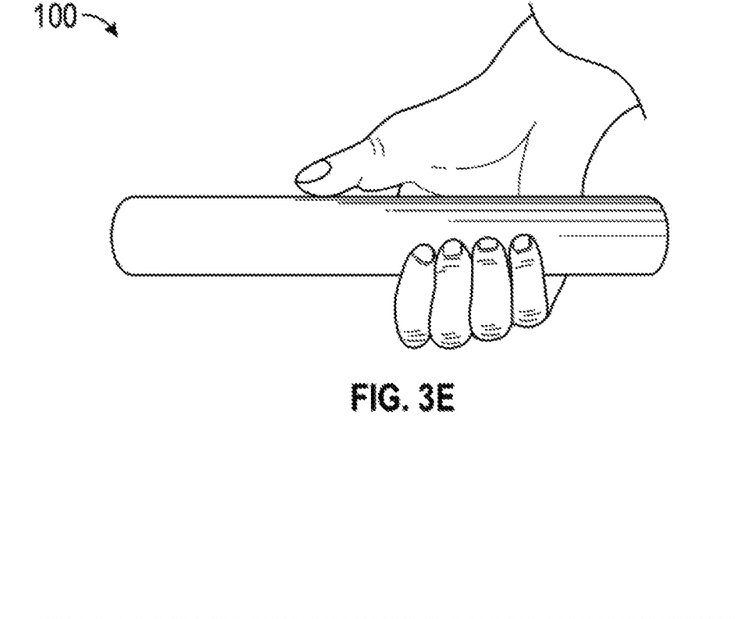

As shown in FIGS. 2A and 2B, the outer sheath 108 can translate along the longitudinal axis L-L over a first range of travel as the first and second arms 106a and 106b pivot about the living hinge 104. This is due to a lost-motion effect achieved by the living hinge 104 which forces the arms 106a and 106b to extend outwardly as living hinge 104 is flattened. In one embodiment, the first range of travel may be approximately 15-20 mm, although this distance may be tailored to any desired value depending on intended use. The longitudinal motion of outer sheath 108 over the first range of travel results from the flattening of living hinge 104. Next, as shown in FIGS. 2B and 2C, once the arms 106a and 106b are generally collinear with the living hinge 104, the outer sheath travel can now translate along a second range of travel as living hinge 104 in its substantially collinear configuration slides within housing 100. Generally, the second range of travel is greater than the first range of travel and may be of sufficient distance to allow full deployment of stent 200 or other medical device.

Figure 4:
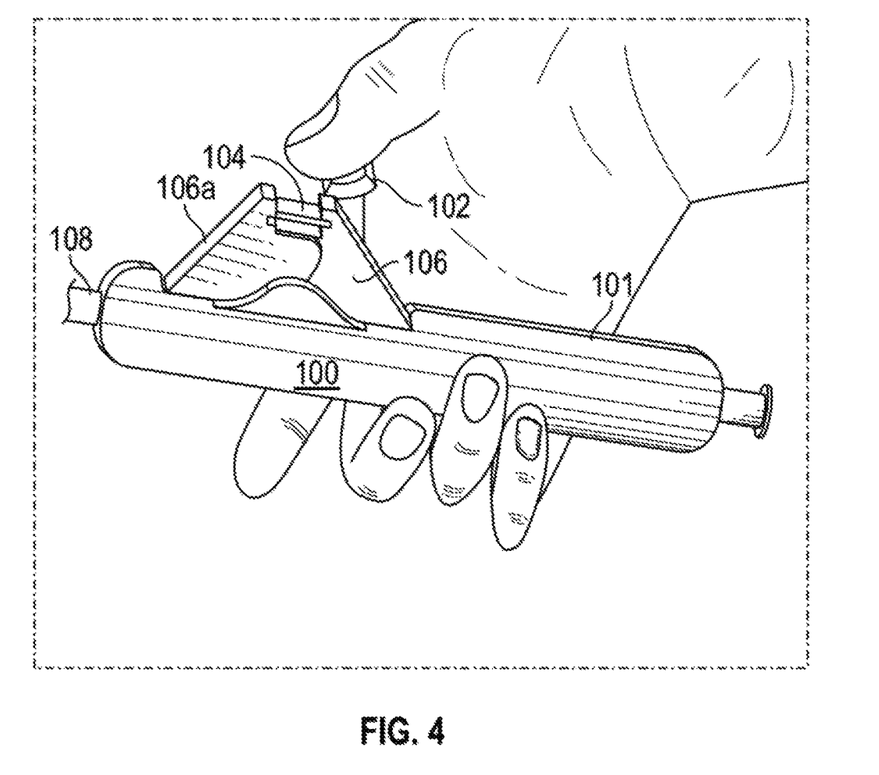
FIG. 4 is a schematic illustration of a medical device delivery system, according to an embodiment.

FIG. 4 schematically illustrates one embodiment that utilizes the various components described earlier in FIGS. 1-3. The living hinge 104 is preferably made from a polymeric material and coupled with a suitable coupling member to the arms 106a and 106b. As well, the living hinge 104 may be an integral part of the first and second arms 106a and 106b. Other materials can be utilized as long as such materials allow for connection between the two arms.

In operation, the distal end of the medical device delivery system 10 is preferably directed into a patient via a body passageway 300 of the patient. The medical device delivery system 10 may preferably follow along a guidewire (not shown) or travel through a previously placed guiding catheter (not shown), until the distal tip 90 is at a desired location in the body vessel 300 for treatment. As shown in FIG. 5A, the distal tip 90 has preferably crossed the site of a lesion or stenosis 302. When the device is properly in an initial position (FIG. 5A), the physician releases or breaks off the lock of the handle (not shown for brevity and not required in all embodiments). The lock may be releasable only once, or may be capable of repeatedly being engaged and released. Such a locking mechanism preferably resists inadvertent or accidental movement or retraction of the stent delivery system components during packaging, sterilization, shipping, storage, handling and preparation.

Figure 5B:
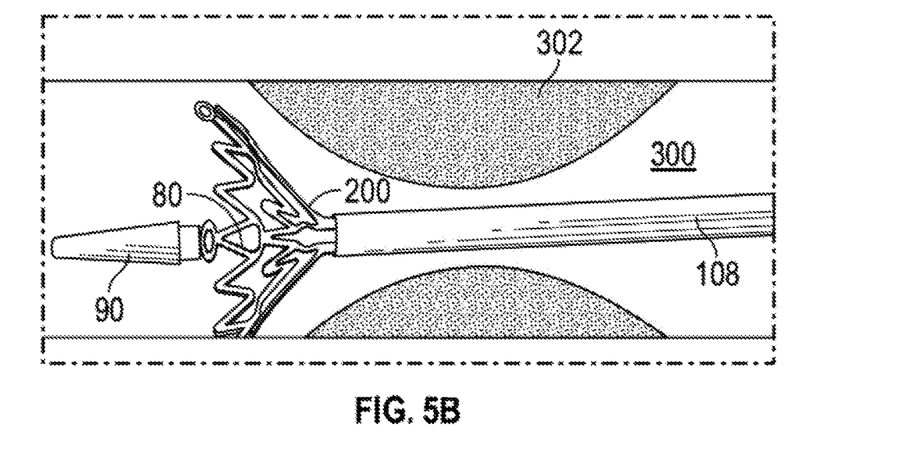

After the lock is released, the thumb actuator 102 can be depressed downward (FIG. 5B) such that the outer sheath 108 is retracted slowly towards the operator due to the lost motion effect of these components. Depression of thumb actuator 102 correspondingly causes outer sheath 108 to translate along axis L-L over the first range of travel. Due to the geometry involved, the distance traveled by thumb actuator 102 as it is moved in a generally orthogonal direction with respect to axis L-L until living hinge 104 is in its collinear configuration is greater than this first range of travel, as the mechanical advantage is less than a 1:1 ratio. In other words, the distance moved by thumb actuator 102 as it is depressed orthogonally may be greater than the longitudinal distance moved by outer sheath 108 over its first range of travel. Correspondingly, the use of these components and this configuration allows precise and sensitive adjustment to pull the outer sheath 108 back slightly. This small movement exposes a small portion of the medical device, in this case a stent 200, as shown in FIG. 5B. In this configuration, the handle 100 will hold the outer sheath 108 in position relative to the inner shaft 80, resisting further inadvertent expansion of the stent 200. The physician then has the time and flexibility of procedure to selectively optimize and make any final adjustments to the position of the medical device and delivery system within the desired site, as illustrated in FIG. 5B. This precise adjustment of the position of the stem 200, before any portion of the stent 200 touches the body passage or vessel 300 in a manner that might inhibit further positional adjustment, is preferable.

Figure 5C:
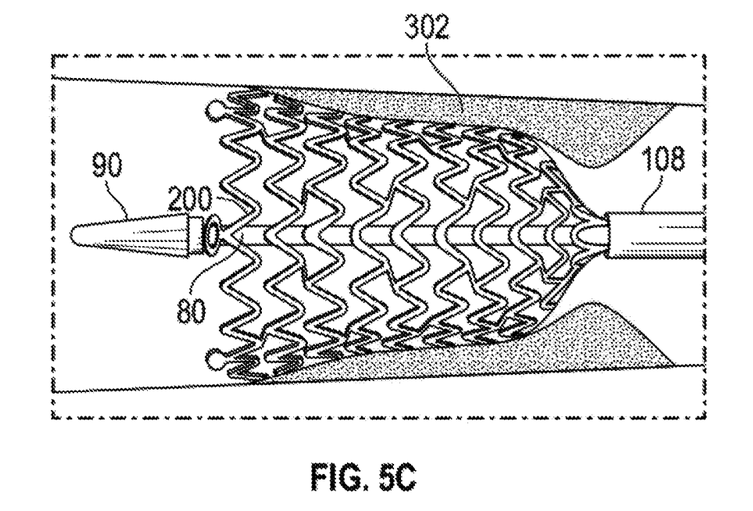

When the physician is satisfied with the positioning, as it appears on a fluoroscopic x-ray video screen for example, the physician may then slide thumb actuator 102 to translate the now collinear living hinge 104 within housing, further withdrawing the outer sheath 108 as shown in FIG. 5C over the second range of travel.

In FIG. 5C, upon initial contact of the stent 200 with the vessel wall, or when the stent is 200 expanded sufficiently to independently hold its position, or at any desired point, the physician continues to pull back on the thumb actuator. This second mode of withdrawing the outer sheath 108 (over the second range of travel) allows relatively large-scale and rapid movement, at whatever speed the physician wishes, to quickly deploy the medical device by completely exposing it. In particular, when living hinge 104 is collinear and is being slid longitudinally rather than being depressed perpendicularly to axis L-L, the mechanical advantage is 1:1 as the movement of thumb actuator 102 is directly translated to movement of outer sheath 108.

Thus, the different mechanical advantages associated with the first and second ranges of travel facilitate moving outer sheath 108 at a first rate of movement (over the first range of travel) that allows for precise exposure and initial deployment of the medical device and at a second, greater rate of movement (over the second range of travel) to complete deployment of the medical device more quickly once the physician is satisfied with its placement. In other words, a given amount of movement of thumb actuator 102 (orthogonally) causes less translation of outer sheath 108 over the first range of travel than the same amount of movement (longitudinally) over the second range of travel. Since relatively less motion of thumb actuator 102 is needed over the second range of travel, the physician may correspondingly withdraw outer sheath 108 more quickly when desired.

Various materials may be selected for the components of the present invention, including any material having the desirable performance characteristics. In the particular embodiment shown in the drawings, the inner and outer shaft members and, strain relief and distal tip may be made of any biocompatible and suitably flexible yet sufficiently strong material, including polymers of various types. Possible selections for such materials include nylons or polyamides, polyimides, polyethylenes, poly urethanes, polyethers, polyesters, etc. In the alternative, some portion or all of the inner and/or outer shaft member may be formed of a flexible metal, including for example stainless steel or nitinol hypotube. The stent 200 is preferably made of any biocompatible material that is strong and rigid, including for example stainless steel, platinum, tungsten, etc. The components of the handle of the present invention are preferably made of a material that is strong and rigid, including for example inflexible polycarbonates, or even some metal components. In addition, the inner shaft member distal tip may preferably be provided with a through lumen adapted to receive a guidewire.

Of course, many different variations are included within the scope of the present invention. Some of these variations or alternative embodiments include any possible arrangement of sizes, materials, and designs within the scope of the claims.

By virtue of the disclosure provided herein, a method of delivering a self-expanding stent to selected location in a body vessel can be utilized. The method can be achieved by: moving a stent to a selected location in a body vessel, the stent being disposed adjacent a catheter tip and confined between an inner shaft and an outer sheath at a distal end of a delivery system; depressing an actuator orthogonally with respect to a longitudinal axis to translate the outer sheath along a longitudinal axis over a first range of travel; and sliding the actuator along the longitudinal axis to translate the outer sheath along the longitudinal axis over a second range of travel depressing an actuator orthogonally with respect to a longitudinal axis to translate the outer sheath over a first range of travel along a longitudinal axis to expose a portion of the stent; and sliding the actuator along the longitudinal axis to translate the outer sheath over a second range of travel along the longitudinal axis to completely deploy the stent. The outer sheath may undergo relatively less translation along the longitudinal axis over a first range of travel for a given amount of movement of the actuator and may undergo relatively greater translation along the longitudinal axis over the second range of travel for the given amount of actuator movement. The outer sheath may be translated at a relatively greater rate over the second range of travel as compared to the first range of travel as desired to facilitate stent deployment.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A stent delivery system comprising:
   a catheter tip coupled to an inner shaft and an outer sheath with a stent disposed between the inner shaft and the outer sheath, the inner shaft and the outer sheath extending from a distal end to a proximal end;
   a housing extending along a longitudinal axis from a first end to a second end, the housing defining a slot in an exterior surface of the housing along the longitudinal axis;
   a first arm coupled to the housing and having a portion of the first arm extending through the slot;
   a second arm connected to the first arm via a living hinge, the second arm coupled to the outer sheath, the second arm having a portion extending through the slot; and
   an actuator member coupled to the first arm.

2. The stent delivery system of claim 1, in which the first arm is coupled to an interior wall proximate the first end of the housing.

3. The stent delivery system of claim 1, in which the second arm is coupled to a pivot mount connected to the outer sheath.

4. The stent delivery system of claim 3, in which the pivot mount is confined to translate in the slot along the longitudinal axis.

5. The stent delivery system of claim 1, in which a luer port is coupled to the outer sheath at the second end of the housing.

6. The stent delivery system of claim 1, in which the outer sheath is configured to translate along the longitudinal axis over a first range of travel as the first and second arms pivot about the living hinge and the outer sheath is configured to translate along the longitudinal axis over a second range of travel when the first and second arms are substantially collinear with the living hinge.

7. The stent delivery system of claim 6, wherein the actuator member is configured to move orthogonally to the longitudinal axis over the first range of travel.

8. The stent delivery system of claim 7, wherein the actuator member is configured to cause less translation of the outer sheath over the first range of travel as compared to the second range of travel for a given amount of actuator member movement.

9. A stent delivery system comprising:
   a housing extending along a longitudinal axis from a first end to a second end, the housing defining a slot in an exterior surface of the housing along the longitudinal axis;
   an outer sheath configured for movement along the longitudinal axis;
   a first arm coupled to the housing and having a portion of the first arm extending through the slot;
   a second arm connected to the first arm via a living hinge, the second arm coupled to the outer sheath, the second arm having a portion extending through the slot; and
   an actuator member coupled to the first arm.

10. The stent delivery system of claim 9, in which the first arm is coupled to an interior wall proximate the first end of the housing.

11. The stent delivery system of claim 9, in which the second arm is coupled to a pivot mount connected to the outer sheath.

12. The stent delivery system of claim 11, in which the pivot mount is confined to translate in the slot along the longitudinal axis.

13. The stent delivery system of claim 9, in which a luer port is coupled to the outer sheath at the second end of the housing.

14. The stent delivery system of claim 9, in which the outer sheath is configured to translate along the longitudinal axis over a first range of travel as the first and second arms pivot about the living hinge and the outer sheath is configured to translate along the longitudinal axis over a second range of travel when the first and second arms are substantially collinear with the living hinge.

15. The stent delivery system of claim 14, wherein the actuator member is configured to move orthogonally to the longitudinal axis over the first range of travel.

16. The stent delivery system of claim 15, wherein the actuator member is configured to cause less translation of the outer sheath over the first range of travel as compared to the second range of travel for a given amount of actuator member movement.

* * * * *